United States Patent [19]
Merz et al.

[11] Patent Number: 6,025,029
[45] Date of Patent: *Feb. 15, 2000

[54] STORAGE STABLE, HUMIDITY CURING ADHESIVES

[75] Inventors: Peter Merz, Wollerau; Roland Dux, Geroldswil; Didier Grichting, Zurich, all of Switzerland

[73] Assignee: Sika AG, vorm. Kasper Winkler & Co., Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/873,128

[22] Filed: Jun. 11, 1997

[30] Foreign Application Priority Data

Jun. 12, 1996 [CH] Switzerland .............................. 1464/96

[51] Int. Cl.$^7$ ................................ B05D 3/02; C08J 3/00; C08K 3/20; C08L 75/00
[52] U.S. Cl. .................................. 427/372.2; 427/385.5; 524/590; 528/53
[58] Field of Search ............................ 524/590; 528/53; 427/372.2, 385.5

[56] References Cited

U.S. PATENT DOCUMENTS

| | | | |
|---|---|---|---|
| 4,705,840 | 11/1987 | Buckanin | 528/53 |
| 4,780,520 | 10/1988 | Rizk et al. | 528/53 |
| 5,195,946 | 3/1993 | Li et al. | 602/8 |
| 5,525,663 | 6/1996 | Oien | 524/590 |

FOREIGN PATENT DOCUMENTS

| | | |
|---|---|---|
| 2624016 | 12/1976 | Germany . |
| 4327498 | 2/1994 | Germany . |
| 2231879 | 11/1990 | United Kingdom . |

*Primary Examiner*—Patrick D. Niland
*Attorney, Agent, or Firm*—Burns, Doane, Swecker & Mathis, L.L.P.

[57] ABSTRACT

A morpholine group comprising catalyst of the general formula,

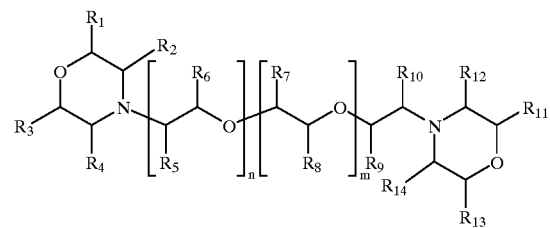

wherein n+m is >1 and $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently from each other hydrogen or an alkyl group, particularly a methyl or an ethyl group, is described. Said catalyst is particularly suitable for the use in storage stable polyurethane (PU)-compositions usable as adhesives, sealings, coatings or pretreatments with a primer. Said PU compositions have a delayed skinning time and thus an extended assembly time but nevertheless a fast development of strength, and they are suitable for the application on metal, glass, ceramics, wood, cementitious substratums and plastic substratums.

18 Claims, No Drawings

STORAGE STABLE, HUMIDITY CURING ADHESIVES

CROSS REFERENCE TO RELATED APPLICATIONS

This application claims the priority of Swiss Application No. 1464/96, filed Jun. 12, 1996, the disclosure of which is incorporated herein by reference in its entirety.

FIELD OF THE INVENTION

The present invention regards a catalyst, particularly a catalyst for usage in polyurethane systems and especially for the use in humidity reactive polyurethanes (PU), its production and its use. Particularly the invention concerns a catalyst which is suitable for being used in adhesive, sealing and coating compositions and pretreatments with a primer, which are storage stable if stored under exclusion of humidity. Said compositions are on the basis of humidity reactive polyurethanes (PU) which are fast curing in the presence of humidity.

BACKGROUND OF THE INVENTION

Adhesive, sealing and coating compositions and pretreatments with a primer on the basis of polyurethane prepolymers which are humidity curing are known and are broadly used for coating, connecting and sealing building and construction materials such as e.g. plastics, glass, ceramics, varnished sheet metals, metals, wood, concrete and other substratums.

Such compositions do advantageously comprise little or no solvents and they contain isocyanate groups comprising prepolymers which are prepared in a known manner by reacting bifunctional or polyfunctional polyols with an excess of diisocyanate or polyisocyanate, whereby the monomers content in the whole formulation is as low as possible, i.e. smaller than 1%, preferably smaller than 0.5%.

In the presence of e.g. humidity, the isocyanate groups of the monomers as well as the isocyanate groups at the ends of the polyurethane (PU) prepolymer chains react with water under formation of an instable carbamic acid group that spontaneously decomposes to amines and carbon dioxides. Said amino group then does fast react with a further isocyanate group under the formation of a urea group. Said cross-linkage reaction causes a molecule growth and leads to a hard or tough elastic composition suitable for adhesive sealing and coating purposes.

By the admixture of catalysts, the reaction of water with isocyanate groups can be accelerated. Known catalysts are titanates, organometal compounds such as e.g. tin or lead compounds that can also be combined with other catalysts, particularly tertiary amines. Generally the catalysts are used in amounts of up to 2% referred to the whole formulation.

If large amounts of catalyst are used to speed up the curing throughout the layer, on the one hand the stability of the PU system is affected, making an application after short storage time impossible due to an enhancement in the viscosity. On the other hand the temperature stability of the cured composition is reduced due to depolymerisation. Desired is a PU system that is still applicable after a storage time of more than 6 months.

U.S. Pat. No. 4,780,520 describes the use of dimorpholinodiethylether (DMDEE) as catalyst for the formulation of a storage stable fast curing PU system, whereby DMDEE is used in an amount of 0.2 to 1.75% referred to the whole composition.

GB patent application No. 2,231,879 shows that the use of 0.2 to 2% of tetramethyl substituted DMDEE also enables the formation of a storage stable PU-system, whereby the strength development at low temperature and low humidity, i.e. at 5° C. and 50% relative humidity, is faster than with a DMDEE catalysed PU-system.

In U.S. Pat. No. 4,705,840 2,2'-dimorpholinylalkylethers are disclosed which at 24° C. and 55% relative humidity show the same early strength as DMDEE, i.e. 7.5 minutes after application of an orthopaedic bandage, at half the concentration of DMDEE, i.e. with 5% by mole.

The use of the above mentioned catalysts for the formulation of fast curing PU systems with fast strength development has the disadvantage that the assembly time is reduced to below 8 to 10 minutes. The assembly time, also termed open time, is defined as the time between the application and the assembling for which a good adhesion is granted. The skinning time according to experience is shorter than or identical with the assembly time and is an efficient method for the approximate determination of the assembly time (see examples).

SHORT DESCRIPTION OF THE INVENTION

The goal of the present invention was to provide catalysts on the basis of morpholine, which catalysts are suitable for the production of fast curing, storage stable PU systems providing a fast strength development at low temperatures and low humidity (e.g. 5° C. and 80% relative humidity or 23° C. and 20% rel. humidity, respectively). Said catalysts provide furthermore, compared to state of the art products, an extended assembly time, i.e. more than 10 minutes, and a good temperature stability.

This goal was achieved by the inventive catalysts of the following formula

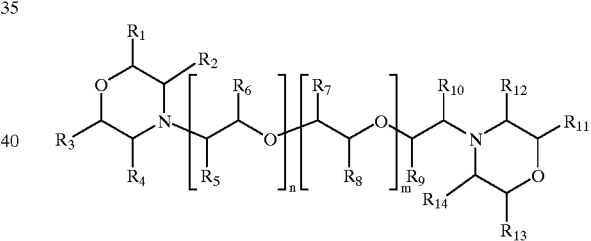

wherein n+m is >1 and wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ independently from each other represent hydrogen or an alkyl group, particularly a methyl group or an ethyl group.

The inventive catalysts primarily enhance the reactivity of the isocyanate groups and therefore are suitable for single-component (sc) systems as well as two-component (tc) systems which cure with water or curing agents on the basis of e.g. reactive OH groups or $NH_2$ groups. The inventive catalysts can be used alone as well as in combination with each other or in combination with known catalysts, e.g. catalysts on the basis of organometallic tin and/or titanium catalysts (see above).

The inventive catalysts are particularly suitable for humidity curing single-component systems.

The effect of the above described morpholine derivatives in humidity curing systems possibly can be seen in that the hydrophilic part—similar to a crown ether—transports water into the matrix and thus in the proximity of the reactive isocyanate groups, and that the two tertiary amines catalytically assist in the reaction of said water with the isocyanate group.

Therefore the inventive catalysts are very suitable for the use in single-component systems. The catalytic effect possibly involves a proton transfer to the amide nitrogen of the isocyanate group (literature thereto: Herlinger Heinz, Habilitationsschrift "Struktur und Reaktivität der Isocyanate", Universität Stuttgart, 1970, p. 24). After the reaction of the isocyanate with water on the one hand carbon dioxide is formed, on the other hand the catalyst, the morpholine derivative, is again liberated. As already mentioned above, this explanation of a possible kind of action is only a probable explanation. Said explanation is not intended to limit the invention in any way.

In a particularly favourable embodiment, the hydrophilic behaviour of the morpholine derivative is enhanced. Said enhancement is achieved by the incorporation of a polyethylene oxide between two morpholine groups. The water absorbing character of the inventive catalysts and therewith the diffusion gradient of the PU system is thus, that the water from the environmental humidity enters the PU composition prior to it being caught by the isocyanate groups present at the surface. Thereby the skinning time is somewhat delayed and the assembly time is extended with simultaneously fast strength development. This combination of features is very advantageous for the user. Furthermore, the traces of water present on the surface of the substratum are transported away from the interface between adhesive and substratum due to the hygroscopic character of the PU composition. Thereby an immediate cross-linking is avoided leading to an improved wetting of the substratum and thereby to improved adhesive properties.

The inventive PU compositions that are catalysed by the inventive catalysts, due to their excellent stability can be processed at enhanced temperatures, i.e. at temperatures up to 95° C., and thus enable the production of storage stable humidity reactive hot melts. Of all one component curing systems such humidity reactive hot melts have the best strength development due to the enhancement in the viscosity upon cooling after application and due to the binder system that is fast curing upon contact with humidity.

The inventive PU compositions are particularly suitable as adhesives, sealings, coating materials and pretreatments with a primer. They exhibit fast strength development and, in comparison with the state of the art, a delayed skinning time and therewith an extended assembly time. They are suitable for the application on metal, glass, ceramics, wood, cementitious and plastic substratums.

DETAILED DESCRIPTION OF THE INVENTION

The inventive catalyst is a morpholine group comprising compound of general formula

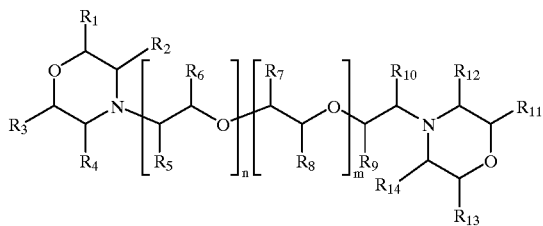

wherein n+m is >1 and $R_1$ to $R_{14}$ are independently from each other either hydrogen or an alkyl group, particularly a methyl group or an ethyl group. In preferred catalysts the sum of n+m is between 2 and 10, particularly between 2 and 5. Specific catalysts that are relatively easy to produce are those, wherein $R_1$ to $R_{14}$ are hydrogen $R_1$ to $R_4$ and $R_9$ to $R_{14}$ are hydrogen and $R_5$ or $R_6$ and/or $R_7$ or $R_8$ are methyl groups, whereby those $R_5$, $R_6$, $R_7$ and $R_8$ which are not methyl groups are hydrogen, $R_1$, $R_3$, $R_{11}$ and $R_{13}$ are methyl groups and $R_2$, $R_4$ to $R_{10}$, $R_{12}$ and $R_{14}$ are hydrogen.

The inventive catalysts can e.g. be produced according to methods of the Canadian patent application 2,103,730 of Miles Inc., USA (1992).

They are especially suitable for the use in isocyanate groups containing single-component polyurethane systems and two-component polyurethane (PU) systems. In particular, the inventive catalysts are very suitable for being used in single-component systems.

The isocyanate groups comprising PU prepolymers which are present in the inventive systems as the main component, are the reaction products of isocyanate groups comprising substances with any compound that is reactive towards isocyanate groups (isocyanate reactive compound). Such compounds are e.g. compounds comprising aliphatic or aromatic polyol groups, polyamine groups or polymercapto groups, whereby the reaction can be performed in known manner at temperatures of about 80° C. and optionally in the presence of a catalyst, e.g. dibutyl tin dilaurate, usually in stoichiometric amounts, i.e. for each group with an active hydrogen one at least two isocyanate groups comprising monomer.

Usually polyols with a functionality of between 1.5 and 3 as well as with a molecular weight of between 400 and 10,000 are used, preferably such polyols with a molecular weight ranging from 1000 to 6000. Such polyols are e.g. polyalkylene polyols (e.g. polyethylene oxide, polypropylene oxide, polybutylene oxide, polytetrahydrofurane), polycarbonates, polycaprolactones, polyesters etc.

The isocyanate groups comprising monomers can be aliphatic, cycloaliphatic or aromatic monomers such as e.g. 4,4'-diphenylmethane diisocyanate, 2,4-toluene diisocyanate, hexamethylene diisocyanate, isophorone diisocyanate, perhydro-2,4'-diphenylmethane diisocyanate etc.

The above described PU prepolymers preferably have a content of free isocyanate in the range of 1 to 3%, and usually the prepolymer is present in amounts referred to the whole composition of 20 to 60%, particularly of 20 to 50%.

The PU-systems of the present invention comprise at least one PU-prepolymer and an inventive curing catalyst.

Said systems optionally can comprise usual additives and adjuvants such as e.g. emollients, fillers, latent curing agents, adhesion promoters, dyes, pigments, UV adsorbers, stabilisers, antioxidants, surface active additives, flame-retardants, fungistatically active substances etc. The kind and amount of said additives or adjuvants is dependent on the intended use of the inventive compositions.

The amount of inventive isocyanate/water curing catalyst generally is in the range of 0.1 to 2% by weight, particularly 0.4 to 1% by weight, referred to the total weight of the composition. While with an amount of below 0.1% the desired curing effect is not achieved, an amount of more than 2% affects the storage stability of the PU-System.

If necessary, the inventive catalysts can be combined with other, conventional catalysts, e.g. organometallic catalysts or catalysts on the basis of tertiary amines.

During the production of the inventive single-component compositions care has to be taken that no humidity is introduced. All components used should largely be free of water and it is appropriate to admix to the PU system water binding or water reactive substances such as e.g. calcium oxide, molecular sieves, monofunctional isocyanate groups comprising compounds ortho formate etc. The ancillary processing is made in known manner with humidity exclusion, e.g. in cartridges, barrels etc.

The inventive PU systems can, according to the requirement, be used for assembling, sealing or coating purposes and have numerous applications in the construction field as well as in industry, e.g. in the vehicle production, the marine etc., whereby application on very different materials such as e.g. glass, ceramics, plastics, PU elastomers, metals and varnished metals, is possible. Possibly a pretreatment with a primer is necessary to get the best possible adhesion.

The invention is further described by means of examples regarding single-component adhesives. These examples however, are not intended to restrict the scope of the invention in any way.

EXAMPLES

Examination of the Storage Stability of the Adhesive Compositions

The viscosity of the adhesive composition was determined by extrusion of a cartridge at 23° C. and with a pressure of 6 bars through a 3 mm nozzle resulting in a value in grams per minute. Said measurement was performed after storage at room temperature for 7 days (=>original extrusion rate), 1 month and 3 months, respectively, as well as after heat ageing at 60° C. for 7 days. Additionally the skinning time was determined for each sample in order to examine the influence of the storage conditions on the reactivity of the adhesive or the curing catalyst, respectively.

Storage of the Specimen

The specimen have been stored under two different climatic conditions, in order to determine the influence of said conditions on the open time and the strength development:

climate I: 23° C. and 50% relative humidity (standard climate), climate II: 5° C. and 80% relative humidity

Determination of the Skinning Time (ST)

The skinning time is the time after application until the sample is track free.

Determination of the Early Strength

The development of the strength was determined using lap shear specimens consisting of two glass plates according to DIN 53504 (cross-head speed: 200 mm/min, thickness of the adhesive layer: 5 mm) after storage of the specimens under the two above defined climatic conditions, whereby the measurement was made after 30 min., 60 min., 90 min. and 3 hours. The value of the lap shear strength (LSS) is indicated in $N/cm^2$.

Catalysts

The following catalysts have been compared:
1. DMDEE (2,2'-dimorpholino ethyl ether) of Nitroil, Germany
2. TMDMDEE (tetra methyl-DMDEE) of Nitroil, Germany
3. DMPEG 200 (dimorpholino polyethylene oxide glycol), (n+m about 3)

While the two catalysts 1 and 2 belong to the state of the art, 3 represents an inventive catalyst (for formula, production, see below).

Formulation of the Adhesive Composition

The kind of action of the catalysts was examined in a standard formulation based, besides of carbon black and chalk, on a prepolymer consisting of a trifunctional polyetherpolyol with a molecular weight of about 4500 and an aromatic isocyanate group comprising monomer, MDI (methylene-4,4'-diphenyl diisocyanate). The amount of catalysts was calculated thus that the morpholine content was 0.4% based on equivalents. This is for DMDEE about 0.5% by weight, for TMDMDEE about 0.4% by weight and for the inventive catalyst DMPEG 200 about 0.8% by weight, all % by weight being referred to the whole adhesive formulation.

Preparation of the Inventive Catalyst DMPEG 200 (According to the Canadian Patent Application CA 2103730/Miles Inc. USA/1992)

A) Production of the Dimesylate of PEG 200

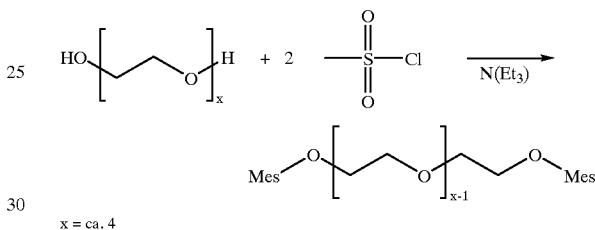

x = ca. 4

11.41 g polyethyleneglycol 200 (Fluka, pract.), 13.1 g triethylamine and 22 ml methylene chloride (Fluka, puriss.) in a 250 ml three-necked flask, provided with reflux condenser, 25 ml dropping funnel and thermometer, are cleansed with nitrogen. Then the mesylchloride is slowly dropped from the dropping funnel into the flask under inert gas and with stirring by means of a magnetic stirrer. Since the reaction taking place is very exothermic, the flask is cooled in iced water and the dropping speed is regulated in a way that the temperature does not exceed 25° C. During the reaction, a white/yellow precipitate is formed. When the dropping has finished, the funnel is washed with 20 ml methylene chloride that are dropped into the flask. The ice water container is omitted and the mixture is stirred for another 1.5 hours at ambient temperature and then carefully neutralised with a concentrated sodium hydroxide solution (5.1 g NaOH (Fluka No. 71691) in 20 ml water). Thereby the precipitate is dissolved leading to a yellow phase. After stirring for another hour, the phase is concentrated using a water jet pump. Thereby the temperature of the water bath is slowly raised to 70° C. (the collecting flask advantageously is cooled with ice water in order to collect the methylene chloride for a further use). During the concentration, again a yellow precipitate is formed. This intermediate was not further purified. The thus obtained intermediate was directly further processed.

B) Production of DMPEG 200

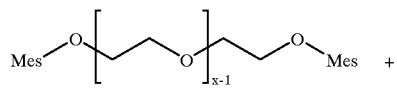

-continued

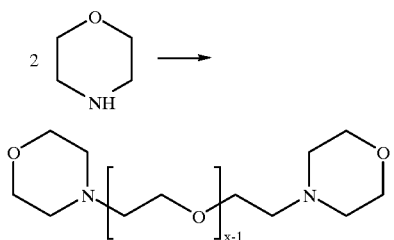

x = ca. 4

The milky residue of the intermediate is diluted with 20 ml methylene chloride and 15.87 g morpholine, 112 ml isopropanol and 20.1 g water free sodium carbonate (Fluka puriss No. 71350) (dried in an oven at 130° C. over night) are added. The reaction mixture is then heated to reflux (bath temperature ~85° C.) and kept at said temperature for about 5 hours. The reaction product is filtered through a glass frit (porosity 4) and separated from a white residue, from which some further small amounts of the product can be separated by ether extraction. The slightly yellow coloured filtrate is then concentrated by means of a water jet pump and then the bath temperature is raised to 80° C. and kept at this temperature for one hour. During said procedure a small amount of solid again precipitates. Said residue now is separated from volatile parts by means of a vacuum generated by a rotary pump during three hours.

Then 100 ml diethyl ether (Fluka purum, F 31700) (PEROXIDE FREE!) are added, the mixture is stirred for 15 minutes and then filtered through a glass frit (porosity 4). The resulting filtrate is concentrated by distilling the ether under ambient pressure and then for one hour at 80° C. bath temperature under a vacuum generated by a water jet pump. The remaining solution is then completely dried under a vacuum generated by a rotary pump (pressure about $10^{-1.5}$ mbar) for 2 hours. About 14.7 g of thus cleaned product DMPEG 200 are obtained corresponding to a yield of about 73%. It comprises less than about 0.04% water (determined by Karl-Fischer titration).

Results of the Comparison Tests

The valuation was made in comparison to the DMDEE-catalysed PU adhesive, whereby the symbols used have the following meaning:

⇒ same performance
⇑ extended skinning time/faster strength development
⇓ shorter skinning time/slower strength development A) ST and Strength Development in Climate I (23° C./15% Relative Humidity (r.h.))

| adhesive with: | DMDEE | TMDMDEE | DMPEG |
|---|---|---|---|
| ST (minutes) | 10 | 10⇒ | 25⇑ |
| LSS after 30' | 6.6 | 6.4⇒ | 7.8⇑ |
| LSS after 60' | 9.4 | 9.5⇒ | 9.7⇒ |
| LSS after 90' | 14.4 | 13.7⇒ | 13.8⇒ |
| LSS after 3 h | 21.5 | 20.8⇒ | 32.1⇑ |

B) ST and Strength Development in Climate II (5° C./80% r.h.)

| adhesive with: | DMDEE | TMDMDEE | DMPEG |
|---|---|---|---|
| ST (minutes) | 17 | 17⇒ | 25⇑ |
| LSS after 30' | 6.7 | 6.5⇒ | 8.7⇑ |
| LSS after 60' | 8.1 | 10.7⇑ | 12.3⇑ |
| LSS after 90' | 9.0 | 11.6⇑ | 13.8⇑ |
| LSS after 3 h | 14.0 | 17.6⇑ | 24.0⇑ |

C. Determination of the Storage Stability

The valuation was made by mentioning the percentual change with regard to the original value. The PU adhesive catalysed with DMDEE, according to experience obtained in practice, has satisfying storage stability.

| Extruded amount | | | |
|---|---|---|---|
| adhesive with: | DMDEE | TMDMDEE | DMPEG |
| 1 month at rt | <20% | <20% | <20% |
| 3 months at rt | <40% | <40% | <40% |

| Skinning Time | | | |
|---|---|---|---|
| adhesive with: | DMDEE | TMDMDEE | DMPEG |
| 1 month at rt | <10% | <10% | <10% |
| 3 months at rt | <10% | <10% | <10% | rt = room temperature

What is claimed is:

1. A method for the production of a sealing, a coating or a pretreatment with a primer wherein a layer of a single-component polyurethane composition is applied on at least one substratum and the layer is cured by ambient humidity, said single-component polyurethane composition comprising at least one prepolymer on the basis of aromatic or aliphatic isocyanate and at least one morpholine groups comprising catalyst of the general formula

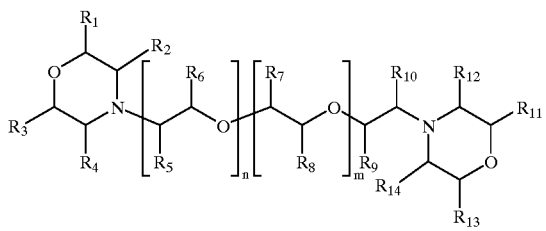

wherein the sum of n+m is between 2 and 10 and $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently from each other hydrogen or an alkyl group.

2. The method of claim 1 wherein in the catalyst the alkyl group is a methyl or an ethyl group.

3. The method of claim 1 wherein in the catalyst the sum of n+m is between 2 and 5.

4. The method of claim 1 wherein in-the catalyst $R_1$ to $R_{14}$ are hydrogen.

5. The method of claim 1 wherein in the catalyst $R_1$, $R_2$, $R_3$, $R_4$, $R_9$, $R_{10}$, $R_{11}$, $R_{12}$, $R_{13}$ and $R_{14}$ are hydrogen and $R_5$ or $R_6$ and $R_7$ or $R_8$ are methyl groups, wherein those of $R_5$, $R_6$, $R_7$ and $R_8$ that are not a methyl group are hydrogen.

6. The method of claim 1 wherein in the catalyst $R_1$, $R_2$, $R_3$, $R_4$, $R_9$, $R_{10}$, $R_{11}$, $R_{12}$, $R_{13}$ and $R_{14}$ are hydrogen and $R_5$ or $R_6$ or $R_7$ or $R_8$ are methyl groups, wherein those of $R_5$, $R_6$, $R_7$ and $R_8$ that are not a methyl group are hydrogen.

7. The method of claim 1 wherein in the catalyst $R_1$, $R_3$, $R_{11}$ and $R_{13}$ are methyl groups and $R_2$, $R_4$, $R_5$, $R_6$, $R_7$, $R_8$, $R_9$, $R_{10}$, $R_{12}$ and $R_{14}$ are hydrogen.

8. The method of claim 1 wherein in the polyurethane composition the catalyst is present in an amount of from 0.1 to 2% by weight referred to the weight of the whole composition.

9. The method of claim 1 which is performed at a temperature of 23° C. or less and a humidity of 80% or less.

10. A method for the production of a joint or a sealing, wherein a layer of a single-component polyurethane composition comprising at least one prepolymer on the basis of aromatic or aliphatic isocyanate and at least one morpholine groups comprising catalyst of the general formula

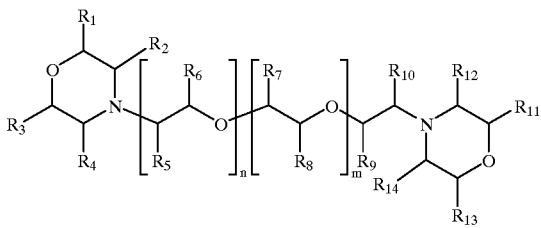

wherein the sum of n+m is between 2 and 10 and $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ are independently from each other hydrogen or an alkyl group, is applied on at least one substratum and the layer is cured by ambient humidity, said substratum being joined to another substratum which is the same or different before the layer becomes tack free.

11. The method of claim 10 wherein in the catalyst the alkyl group is a methyl or an ethyl group.

12. The method of claim 10 wherein in the catalyst the sum of n+m is between 2 and 5.

13. The method of claim 10 wherein in the catalyst $R_1$ to $R_{14}$ are hydrogen.

14. The method of claim 10 wherein in the catalyst $R_1$, $R_2$, $R_3$, $R_4$, $R_9$, $R_{10}$, $R_{11}$, $R_{12}$, $R_{13}$ and $R_{14}$ are hydrogen and $R_5$ or $R_6$ and $R_7$ or $R_8$ are methyl groups, wherein those of $R_5$, $R_6$, $R_7$ and $R_8$ that are not a methyl group are hydrogen.

15. The method of claim 10 wherein in the catalyst $R_1$, $R_2$, $R_3$, $R_4$, $R_9$, $R_{10}$, $R_{11}$, $R_{12}$, $R_{13}$ and $R_{14}$ are hydrogen and $R_5$ or $R_6$ or $R_7$ or $R_8$ are methyl groups, wherein those of $R_5$, $R_6$, $R_7$ and $R_8$ that are not a methyl group are hydrogen.

16. The method of claim 10 wherein in the catalyst $R_1$, $R_3$, $R_{11}$ and $R_{13}$ are methyl groups and $R_2$, $R_4$, $R_5$, $R_6$, $R_7$, $R_8$, $R_9$, $R_{10}$, $R_{12}$ and $R_{14}$ are hydrogen.

17. The method of claim 10 wherein in the polyurethane composition the catalyst is present in an amount of from 0.1 to 2% by weight referred to the weight of the whole composition.

18. The method of claim 10 which is performed at a temperature of 23° C. or less and a humidity of 80% or less.

* * * * *